United States Patent

Shimada et al.

[11] Patent Number: 5,612,495
[45] Date of Patent: Mar. 18, 1997

[54] NON-DESTRUCTIVE EXAMINATION DEVICE

[75] Inventors: Takashi Shimada; Takahiro Sakamoto; Ryosuke Taniguchi; Shinichi Hattori; Noritaka Egami, all of Nagasaki, Japan

[73] Assignee: Mitsubishi Denki Kabushiki Kaisha, Tokyo, Japan

[21] Appl. No.: 539,962

[22] Filed: Oct. 6, 1995

[30] Foreign Application Priority Data

Jun. 9, 1995 [JP] Japan .................................. 7-143731

[51] Int. Cl.⁶ ............................................. G01H 1/00
[52] U.S. Cl. .................. 73/579; 73/643; 73/602; 73/578; 73/628
[58] Field of Search .................. 73/643, 579, 584, 73/596, 602, 627, 628, 577, 578

[56] References Cited

U.S. PATENT DOCUMENTS

| | | | |
|---|---|---|---|
| 4,184,374 | 1/1980 | Thompson et al. | 73/640 |
| 4,307,615 | 12/1981 | Robinson | 73/643 |
| 4,314,479 | 2/1982 | Spijkerman | 73/643 |
| 4,348,903 | 9/1982 | Sato et al. | 73/643 |
| 4,471,658 | 9/1984 | Morimoto | 73/643 |
| 4,481,824 | 11/1984 | Fujimoto et al. | 73/643 |
| 5,170,666 | 12/1992 | Larsen | 73/571 |
| 5,195,046 | 3/1993 | Gerardi et al. | 73/583 |
| 5,457,994 | 10/1995 | Kwun et al. | 73/587 |

FOREIGN PATENT DOCUMENTS 48-66982  9/1973  Japan .

OTHER PUBLICATIONS

A. Nagamatsu, "Structure of Representative Vibration Test System", *Introduction to Modal Analysis*, Chapter 5, pp. 220–301.

Primary Examiner—Hezron E. Williams
Assistant Examiner—Richard A. Moller
Attorney, Agent, or Firm—Burns, Doane, Swecker & Mathis, LLP

[57] ABSTRACT

A non-destructive examination device has an excitation current generation device for supplying an excitation current based on a control signal from a control device, a vibration excitor device for generating an elastic wave in accordance with athe excitation current and for vibrating an examination target to be examined by using the elastic wave; a response detection device (an acceleration sensor) for detecting a response of the vibration of the examination target caused by the elastic wave and for processing the response data in order to select desired examination information. The excitation current generation device generates the excitation current of an alternating pulse wave such as a pulse wave, or a rectangular wave, or a triangular wave, or a sine wave based on the control signal which is also a pulse signal. It can be acceptable to incorporate a plurality of the vibration excitor devices on the examination target in the non-destructive examination device.

15 Claims, 8 Drawing Sheets

NON-DESTRUCTIVE EXAMINATION DEVICE

BACKGROUND OF THE INVENTION

1. Field of the Invention

The present invention relates to a non-destructive examination device for examining fatigue or state of breaking of structure such as architectures, bridges, and machines called as "examination targets" to use an elastic wave, for example.

2. Description of the Prior Art

A vibration examination is an important technology for a structure design, where the vibration examination examines the states of fatigue and breaking of the examination target and estimates mechanical strength of them in order to design an optimum structure thereof.

A main object of the vibration examination is to identify a dynamic character and a vibration mode of an examination target. The non-destructive examination device used for the vibration examination generates a vibration and provides the generated vibration to the target to vibrate it. It then measures the response information of the magnitude of the generated vibration in the examination target, echo transmitted from the examination target, and a vibration state of the examination target. Then, it processes the response information as measured results and obtain required information of the examination target.

There are conventional methods in the prior art to provide the vibration to the examination target, for example a vibration exciter device as a first method, and an impact hammer as a second method which have been described in a literature, "MODE ANALYSIS INTRODUCTION", NAGAMATU AKIO, pages 221–228, CORONA publishing CO., LTD.

There are mechanical vibration exciter devices such as an electrical type oil hydraulic vibration exciter device, a piezo electric vibration exciter device, and a conductive vibration exciter device. The mechanical vibration exciter devices use an internal force as a drive force generated by mechanical motion. The electrical type oil hydraulic vibration exciter has oil hydraulic cylinders and oil hydraulic valves whose opening and closing are controlled electrically in order to move the oil hydraulic cylinders. The piezo electric vibration exciter utilizes a piezo electricity effect. The conductive vibration exciter utilizes Lorentz's force acting on a current in a magnetic field.

However, to use these conventional vibration exciter devices, they must be attached on an examination target to examine it and the examination target must be processed in order to attach the vibration exciter device. These methods lack application flexibility. In addition, the mass of the vibration exciter device to be attached on the examination target affects the dynamic characteristics of the examination target. This is unavoidable. This is a problem.

An impact hammer is widely used for vibrating an examination target.

Figure 1:
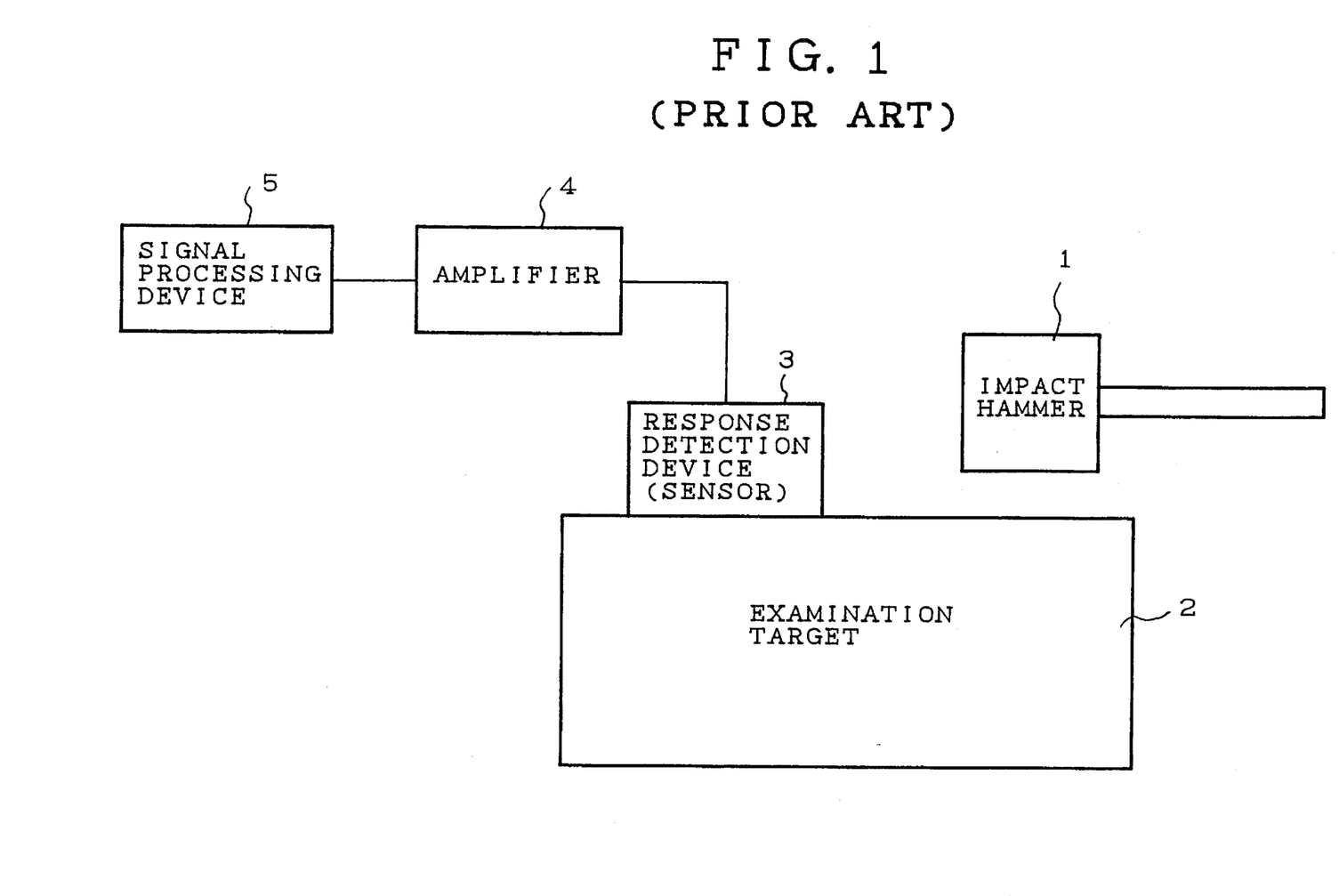
FIG. 1 is a block diagram showing a configuration of a conventional non-destructive examination device.

FIG. 1 illustrates a block configuration diagram of a conventional non-destructive examination device using an impact hammer which has been disclosed in the previous literature.

In FIG. 1, a reference number 1 designates an impact hammer, 2 denotes a examination target to be examined, 3 denotes a response detector device, 4 denotes an amplifier for amplifying an output signal transmitted from the response detector device 3, and 5 designates a signal processing device for extracting and selecting required examination data by processing the amplified output signal form the amplifier 4.

Next, the operation of the conventional non-destructive vibration exciter device shown in FIG. 1 will now be explained.

A vibrational response generated in the examination target which has been vibrated by the impact hammer 1 is detected and converted to an electric signal by the response detector device such as an acceleration sensor. The converted electric signal is amplified by the amplifier 4 and then transferred to the signal processing device 5. In the signal processing device 5, the electric signal received is processed using processes such as a high speed Fourier transformation process, or an integral process. Then, the evaluation or estimation of the state of the examination target 2 is performed based on the result obtained by the above processes.

An operator performs the addition of the vibration to the examination target 2 by using the impact hammer 1. Because an impact operation time period in which the operator adds the vibration to the examination target 2 by using the impact hammer 1 is short and the operator can perform it relatively easy, it is widely used to evaluate the state of the examination target 2. However, it is required for the operator to have a high skill level and a highly technical background in order to use the conventional non-destructive examination device shown in FIG. 1.

SUMMARY OF THE INVENTION

This invention is invented to solve the problems caused in the conventional non-destructive examination device described above.

An object of the present invention is to provide a non-destructive examination device which is capable of repeatedly vibrating an examination target with a constant force, of vibrating a plurality of points on the examination target at the same time, and of easily controlling the magnitude of a strength of the vibration, a vibration frequency to be added to the examination target, without any highly-skilled operator and/or operator with a highly technical background.

In accordance with one aspect of the present invention, there is provided a device a non-destructive examination device, comprising:

excitation current generation means for generating an excitation current and supplying said excitation current;

control means for generating a control signal to control operation of said excitation current generation means and for transmitting said control signal to said excitation generation means;

vibration excitor means for receiving said excitation current and for generating an elastic wave in accordance with a magnitude of said excitation current and for vibrating an examination target to be examined by using said elastic wave;

response detection means for detecting a vibration of said examination target responding to said elastic wave and for transforming said vibration to an electrical signal and for providing said electrical signal; and signal processing means for receiving said electrical signal and for processing said electrical signal in order to obtain desired examination information.

Accordingly, by using the non-destructive examination device, the elastic wave is generated by the vibration excitor device in accordance with the excitation current provided from the excitation current generation device, and then the response signal from the examination target which has been vibrated by the elastic wave is detected by the response detector. The signal processing device processes the response signal from the response detector to obtain or select the required detection data. Accordingly, the magnitude, the frequency, and the waveform of the vibration to be added to the examination target can be controlled with desired values, so that a constant magnitude force of the vibration can be added to the examination target in order to obtain a vibration exciter result with a high accuracy.

In addition, in the non-destructive examination device of the present invention, said excitation current generation means provides said excitation current of a pulse phase to said vibration exciter means in accordance with said control signal. Accordingly, the excitation current of the pulse phase (or the excitation current pulse) is supplied to the vibration exciter device, so that rapid impact vibration whose force is more than that of the impact hammer can be added to the examination target.

In the non-destructive examination device of the present invention, said excitation current generation means provides said excitation current of alternating wave phase such as a sine wave phase, a rectangular wave phase, or a triangle wave phase to said vibration exciter means in accordance with said control signal. Thereby, the amplitude of the excitation current can be increased in order to generate the vibration force to the examination target.

In the non-destructive examination device of the present invention, said signal processing means receives said excitation current generated by said excitation current generation means, and adds and averages said electrical signal provided from the response detection means at a constant timing rate in accordance with the vibration of said vibration exciter means imparted to said examination target based on a trigger generated when said excitation current is detected.

Thereby, the response detection signal from the response detection device is added and averaged at a constant time interval by using the excitation current as a trigger, so that a Signal/Noise (S/N) ratio can be increased.

In the non-destructive examination device of the present invention, said vibration exciter means comprises a plurality of vibration exciter devices which have a same configuration and a same function, said excitation current generation means provides said excitation current to said plurality of vibration exciter devices, said plurality of vibration exciter devices receive said excitation current in synchronization with each other, and each of said plurality of vibration exciter devices generates said elastic wave in accordance with said excitation current. Thereby, the excitation current is provided to a plurality of vibration exciter devices and the plurality of vibration exciter devices generates elastic waves which are in synchronism with each other, so that a vibration force having a great magnitude can be added to any desired point on the examination can be obtained target. In addition, the results of the vibration exciter examination with higher accuracy because a plurality of points on the examination target can be vibrated at the same time and in synchronization with each other.

Furthermore, the non-destructive examination device of the present invention further comprises amplifier means located between said excitation current generation means and said vibration exciter means for amplifying said excitation current and for generating an excitation current having a desired magnitude, and for providing said amplified excitation current to said vibration exciter means.

Moreover, the non-destructive examination device of the present invention further comprises a plurality of amplifier means located between said excitation current generation means and said plurality of vibration exciter devices, each of said plurality of amplifier means connected to one of said plurality of vibration exciter devices, said plurality of amplifier means amplifying said excitation current and each of said plurality of amplifier means generating an excitation current having a desired magnitude and providing said amplified excitation current to each of said plurality of vibration exciter devices.

In the non-destructive examination device of the present invention, said vibration exciter means comprises a magneto striction vibrator having a hollow body and an excitation coil wound around said hollow body, and said magneto striction vibrator vibrates when said excitation current flows in said excitation coil.

In the non-destructive examination device of the present invention, a resonant frequency of said excitation current flowing said excitation coil is determined by a propagation speed of said vibration propagated in said magneto striction vibrator and a shape of said magneto striction vibrator.

In the non-destructive examination device of the present invention, a full length of said magneto striction vibrator is several times a ¼ wavelength of said resonant frequency.

In the non-destructive examination device of the present invention, the magnitude and the frequency of said excitation current is changed by said control signal generated by said control means.

In the non-destructive examination device of the present invention, said magneto striction vibrator having a laminate structure comprises a plurality of thin plates of a magneto striction material, and a laminate direction of said plurality of thin plates of said magneto striction vibrator and a vibration direction of said magneto striction vibrator cross at right angles.

In the non-destructive examination device of the present invention, said magneto striction vibrator has a laminate structure comprises a plurality of thin plates of a magneto striction material of Nickel (Ni).

In the non-destructive examination device of the present invention, said magneto striction vibrator has a laminate structure comprises a plurality of thin plates of a magneto striction material of Cobalt-Iron (Co-Fe).

These and other objects, features, aspects and advantages of the present invention will become more apparent from the following detailed description of the present invention when taken in conjunction with the accompanying drawings.

DESCRIPTION OF THE PREFERRED EMBODIMENTS

The present invention will now be described in detail in conduction with exemplary or preferred embodiments by reference to the accompanying drawings.

First Embodiment

Figure 2:
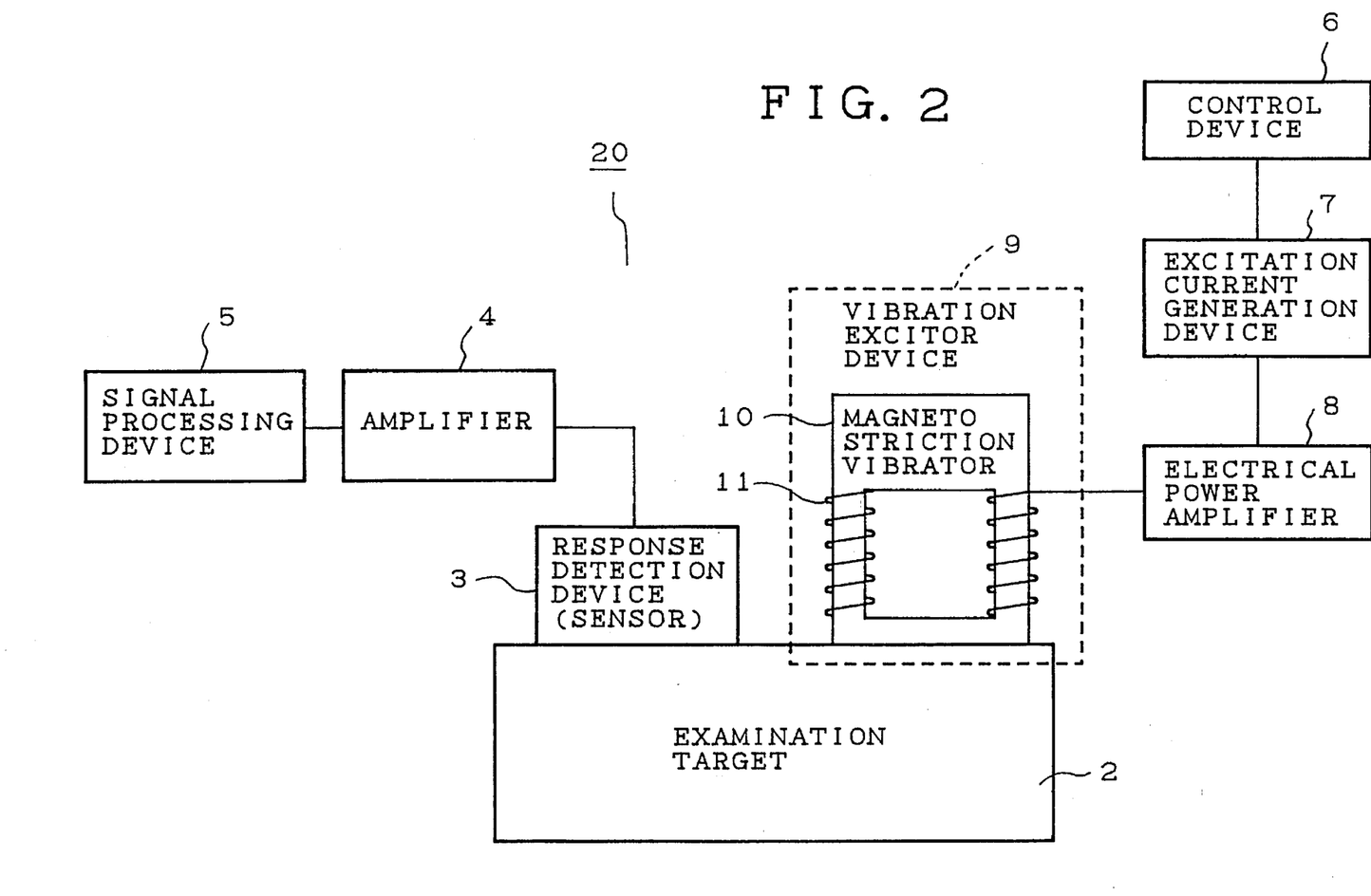
FIG. 2 is a block diagram showing a configuration of a non-destructive examination device as a first embodiment of the present invention.

FIG. 2 is a block diagram showing a configuration of a non-destructive examination device 20 as a first embodiment of the present invention.

In FIG. 2, configuration components that are the same as the configuration components of the non-destructive examination device shown in FIG. 1 are designated by the same reference numbers and the explanations therefor are omitted here.

In FIG. 2, a reference number 6 designates a control device generating a control signal, for example a control signal pulse and transmitting it to another device. The reference number 7 denotes an excitation current generation device for receiving the control signal pulse from the control device 6 and generating an excitation current. The reference number 8 designates an electric power amplifier device (or a power amplifier) for amplifying the excitation current. The reference number 9 denotes a vibration exciter device for receiving the amplified excitation current as an output signal from the power amplifier 8 and generating an elastic wave, and vibrating the examination target 2 with the elastic wave. The vibration exciter device 9 comprises a magneto striction vibrator 10 and an excitation coil 11. The non-destructive examination device 20 of the first embodiment comprises the components 3, 4, 5, 6, 7, 8, and 9 excepting the examination target 2. The response detector device 3 is a sensor or such as an acceleration sensor, a displacement sensor. The amplifier 4 amplifies the output signal transmitted from the response detector device 3, and the signal processing device 5 extracts and selects the required examination data by processing the amplified output signal from the amplifier 4.

Figure 3A:
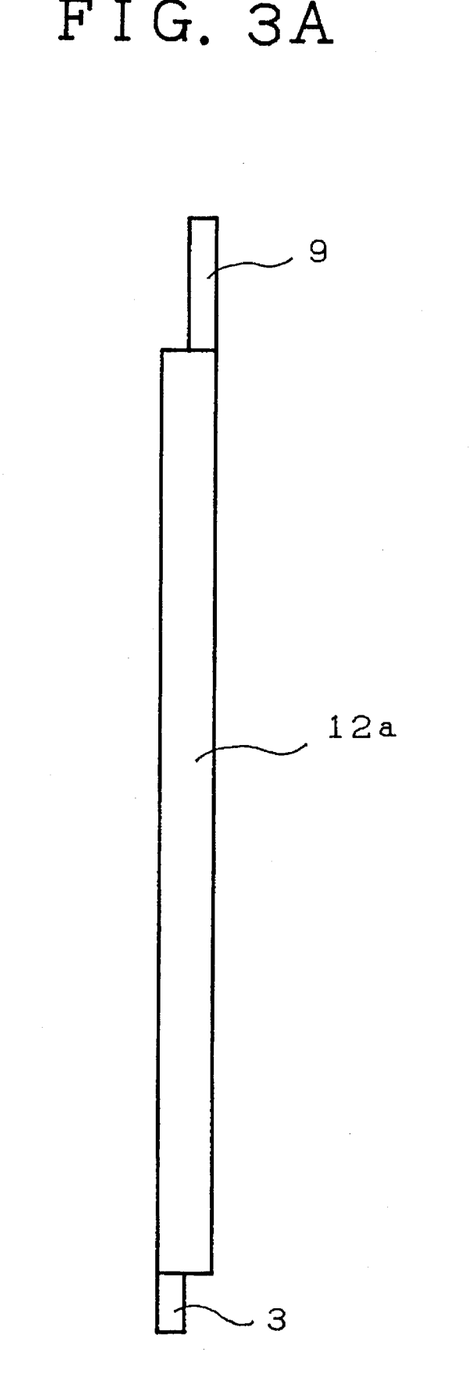
FIGS. 3A and 3B are drawings showing the appearance of non-destructive examination target models to be examined by the non-destructive examination device shown in FIG. 2.
Figure 3B:
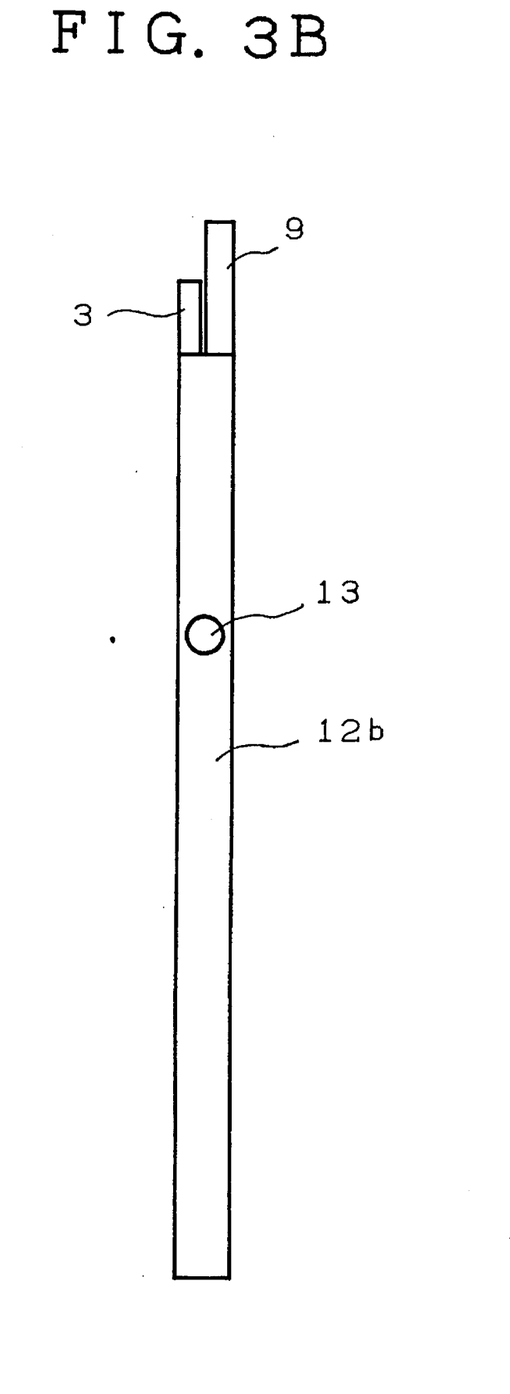

FIGS. 3A and 3B are drawings showing the appearance of non-destructive examination target models 12a and 12b as examination target 2 to be tested by the non-destructive examination device shown in FIG. 2. A reference number 13 designates a circular defect in the non-destructive examination target modes 12b. In FIGS. 3A and 3B, it is shown that the response detector device 3 is connected to the examination targets 12a and 12b as the models to be examined by the non-destructive examination device 20.

Figure 4A:
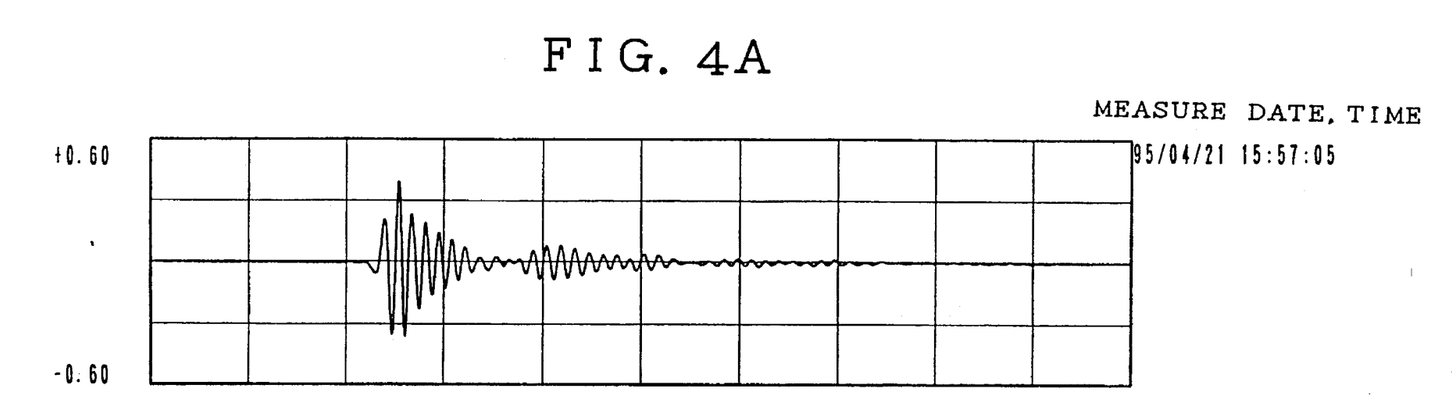
FIGS. 4A and 4B are characteristic drawings showing the results obtained from the vibration test of the non-destructive examination target models shown in FIG. 3A executed by the non-destructive examination device shown in FIG. 2.
Figure 4B:
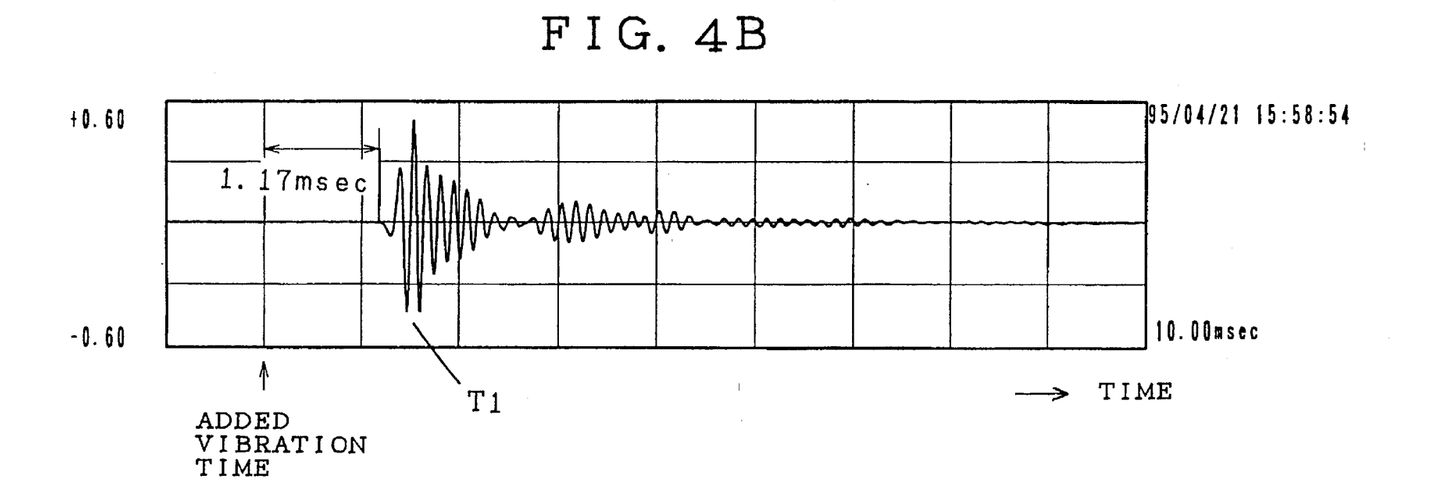
Figure 5:
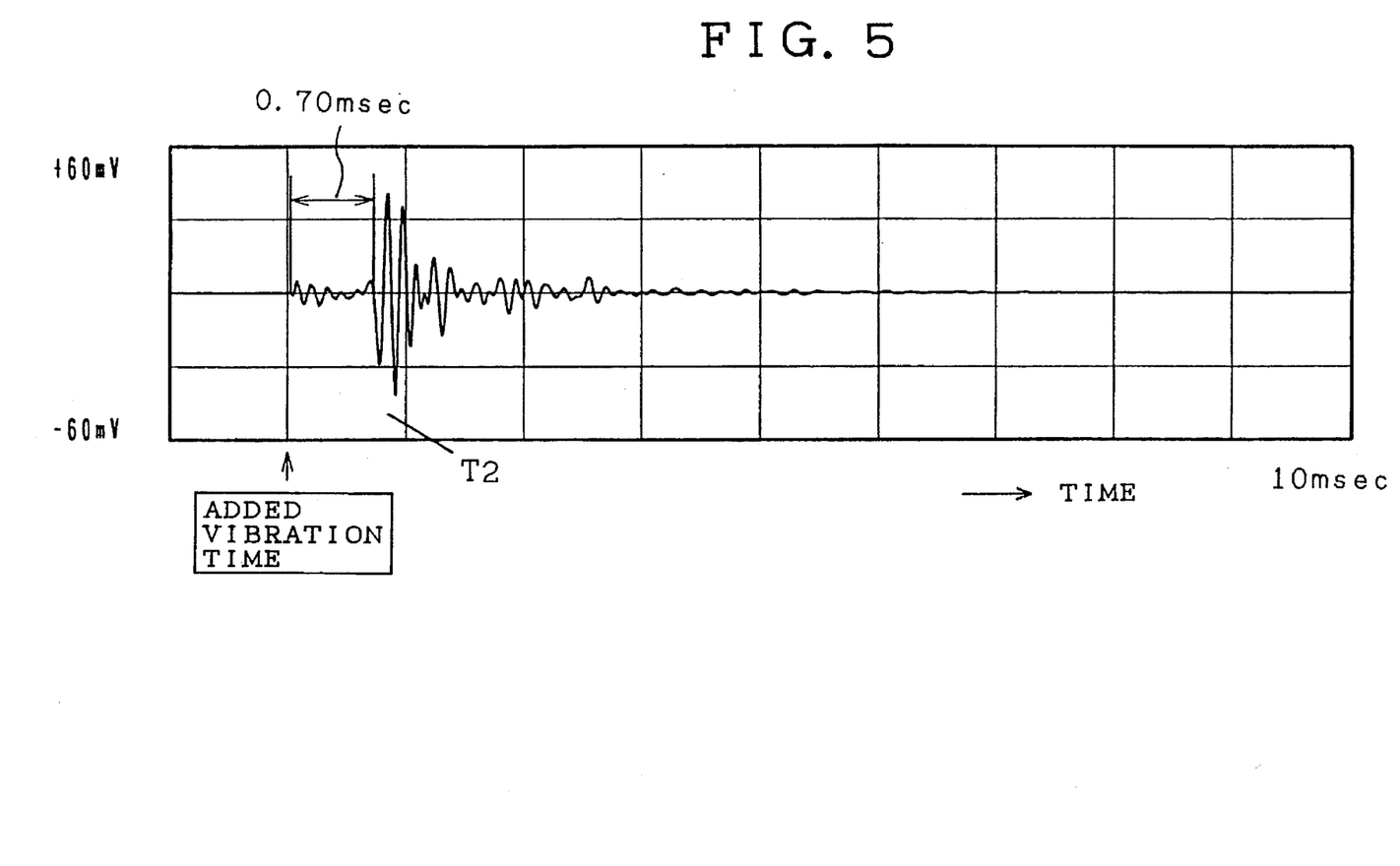
FIG. 5 is a characteristic drawing showing the result obtained from the vibration test of the non-destructive examination target model shown in FIG. 3B executed by the non-destructive examination device shown in FIG. 2.

FIGS. 4A and 4B, and FIG. 5 are characteristic drawings showing the results obtained from the vibration test of the examination targets 12a and 12b shown in FIGS. 3A and 3B executed by the non-destructive examination device 20 shown in FIG. 2.

The graph shown in FIG. 4A shows a response wave when the non-destructive examination target model 12a shown in FIG. 3A is vibrated by using an excitation current pulse generated by the non-destructive examination device 20 (at 15:57:05 on Apr. 21, 1995).

The graph shown in FIG. 4B shows a response wave when the non-destructive examination target model 12a shown in FIG. 3A is vibrated by using an excitation current pulse generated by the non-destructive examination device 20 at another time (at 15:58:54 on Apr. 21, 1995) of the case shown in FIG. 4A.

The graph shown in FIG. 5 shows a response wave when the non-destructive examination target model 12b shown in FIG. 3B is vibrated by using an excitation current pulse generated by the non-destructive examination device 20.

Next, the operation of the non-destructive examination device 20 of the first embodiment of the present invention will now be explained.

Under the condition that the operation of the excitation current generation device 7 is controlled by the control device 6, the excitation current is generated by the excitation current generation device 7.

The electric power amplifier device 8 amplifies the excitation current and provides the amplified excitation current to the excitation coil 11 in the vibration exciter device 9. In this case, a magnetic field is generated around the excitation coil 11 by the excitation current flowing in the excitation coil 11. At this time, a strain of the magneto striction vibrator 10 is caused based on the magneto striction phenomenon. The examination target 2 is vibrated by using the elastic wave generated by the magneto striction phenomenon. In this case, there is no problem about the response speed of the strain caused in the examination target 2 to the change of the excitation current, because the response speed has a range of less than in tens micro seconds which has already been detected by a vibration exciter examination. The response speed is adequately higher within several micro seconds. In addition, a resonance frequency of the excitation current flowing in the excitation coil 11 is determined by the elastic wave transmitted in a magneto striction material forming the magneto striction vibrator 11 and the shape of the magneto striction vibrator 11. The full length of the magneto striction vibrator 11 is approximately several times of ¼ of the wavelength of the resonant frequency. It can be operated to drive the magneto striction vibrator 10 of in tens cm in length with a several kw by using several KHz. Specifically, in this case, the vibration of an optional frequency range can be generated by changing the shape of the magneto striction vibrator 10.

Therefore a desired optional vibration waveform can be generated by controlling the waveform of the elastic wave generated from the vibratory excitor device 9, and the magnitude and the frequency of the excitation current provided from the excitation current generation device 7.

The magneto striction vibrator 10 comprises a magneto striction material of a negative magneto striction constant. For example, the negative magneto striction material is a material mainly including Nickel (Ni).

Thus, the vibration travels to the examination target 2 from the magneto striction vibrator 10 by utilizing the phenomenon that the magneto striction vibrator 10 is rapidly elongated to its original length after it is contracted.

In addition, when the magneto striction vibrator 10 comprises a magneto striction material of a positive magneto striction constant, for example mainly comprising Cobalt-Iron (Co-Fe), the vibration travels to the examination target 2 from the magneto striction vibrator 10 by utilizing the phenomenon that the magneto striction vibrator 10 is rapidly contracted to its original length after it is elongated.

In order to decrease the eddy current loss of the magneto striction vibrator 10 by the excitation current, the magneto striction vibrator 10 is commonly formed with a lamination structure of thin plates. The lamination direction in the magneto striction vibrator 10 is the same as the vibration direction thereof, so that the vibration phase and the magnitude of the vibration of the magneto striction vibrator 10 are changed in synchronization with the frequency of the elongation and contraction thereof. Accordingly, in the non-destructive examination device 20, the strength of the vibration excitor device can adequately be kept because there is no stress to separate the contact between the vibration excitor device 9 and the examination target 2.

When the waveform of the excitation current is a pulse form, the vibration excitor device 9 can rapidly generate a vibration force supplied to the examination target 2 based on the magnitude of the excitation current. A magnitude of the vibration force obtained in this case shown in FIGS. 2–5 is the same as that obtained by the impact hammer 1 in the case shown in FIG. 1. In addition, in the case of the first embodiment of the present invention shown in FIGS. 2–5, the vibration of the constant magnitude can be added to the examination target 2 without any highly-skilled workers or workers having a technical background. Accordingly, the evaluation of the result obtained by the non-destructive examination device 20 can be standardized.

Accordingly, when the examination target model 12a shown FIG. 3A is vibrated by using the excitation current pulse, the characteristic result as the response waveforms shown in FIGS. 4A and 4B relative to the excitation current pulse are obtained.

Both characteristics shown in FIGS. 4A and 4B are different in waveform, but the response waveforms obtained from the cases shown in FIGS. 4A and 4B are the same with respect to each other. Therefore the vibration force having the same magnitude to be added to the examination target can be reproduced by using the non-destructive examination device.

In the characteristics drawings, as shown FIGS. 4A and 4B, the wave packet T1 designates a reflected wave from one end portion of the examination target model 12a. The speed of the reflected wave is 854 m/sec which is obtained by considering a delay time interval after the vibration exciter device 9 adds an impact vibration force to the examination target model 12a.

Next, FIG. 5 shows the response waveform of the examination target model 12b in a case where there is a circular defect 13 in the examination target model 12b. In this case, the reflected wave T2 from the circular defect 13 is apparently shown in FIG. 5. The position of the circular defect 13 from the end portion of the examination target model 12b is 29.9 cm which is calculated based on the propagation speed and the delay time of the vibration by the vibration exciter device 9. This result is approximately the same as the actual distance from the end portion of the examination target model 12b.

The wave of the vibration generated by the vibration exciter device which is bonded on the examination target 2 is propagated to the examination target 2. The vibration exciter device 9 can be used in a condition that the vibration exciter device 9 is not directly bonded to the examination target 2 so long as it is kept that the vibration exciter device 9 is strongly bonded on the examination target 2. Therefore, it can be used easily like the conventional non-destructive examination device shown in FIG. 1 using the impact hammer 1. In addition, the great vibration force can be added and propagated to the examination target 2 because it is no problem structurally to increase the stress of the bonding between the vibration exciter device 9 and the examination target 2.

Second Embodiment

Figure 6:
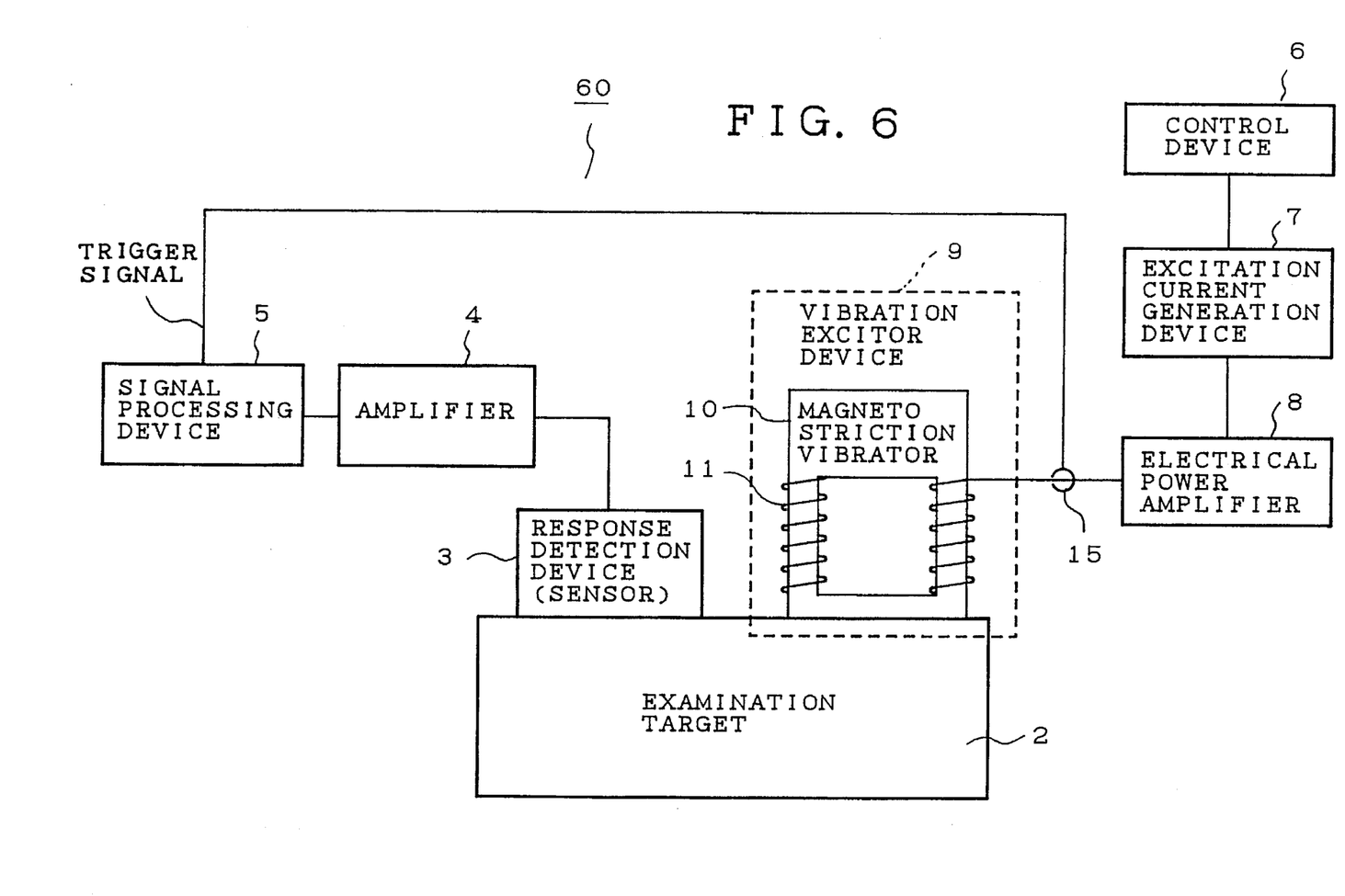
FIG. 6 is a block diagram showing a configuration of a non-destructive examination device as a second embodiment of the present invention.

FIG. 6 is a block diagram showing a configuration of a non-destructive examination device 60 as a second embodiment of the present invention. In FIG. 6, the configuration components that are the same as the configuration components of the non-destructive examination device 20 as the first embodiment shown in FIG. 2 are designated by the same reference numbers and the explanations therefor are omitted here.

A reference number 15 designates an excitation current detector which is placed at an output terminal portion of the electric power amplifier 8.

The other components such as the response detection device 3, the amplifier 4, the signal processing device 5, the control device 6, the excitation current generation device 7, the power amplifier 8, and the vibration excitor device 9 are the same as that of the first embodiment shown in FIG. 2 in configuration and function.

Next, the operation of the non-destructive examination device 60 of the second embodiment shown in FIG. 6 will now be explained.

The control device 6 controls the operation of the excitation current generation device 7. Thereby, the excitation current is generated by the excitation current generation device 7. The power amplifier 8 receives the excitation current from the excitation current generation device 7, and amplifies the excitation current and the provides the amplified excitation current to the excitation coil 11. A magnetic field is generated around the excitation coil 11. The magnetic strain is caused in the magneto striction vibrator 10 in accordance with the magnitude of the magnetic field.

In this case, the response speed of the strain generated in the magneto striction vibrator 10 becomes a constant rate based on the material of the magneto strain vibrator 10.

The excitation current flowing from the power amplifier 8 to the vibration excitor device 9 is detected by the excitation current detector 15. In this case, when a response waveform is recorded based on a trigger which is generated by detecting the excitation current at the excitation current detector 15, the response waveform can be detected with a constant timing rate like the characteristic diagrams as shown in FIGS. 4A and 4B.

The amplifier 4 amplifies the output signal transmitted from the response detector device 3, and the signal processing device 5 extracts the required examination data by processing the amplified output signal from the amplifier 4 based on the trigger signal from the excitation current detector 15.

Accordingly, when the response waveform is added at each constant timing rate by adding the impact vibration by the vibration excitor device 9, and the added response waveforms are averaged, irregular noises in the response waveform can be eliminated from the added response waveforms without strain of the response waveform, and only a weak response signal in the response waveform and the noise can be selected or extracted.

Third Embodiment

Figure 7:
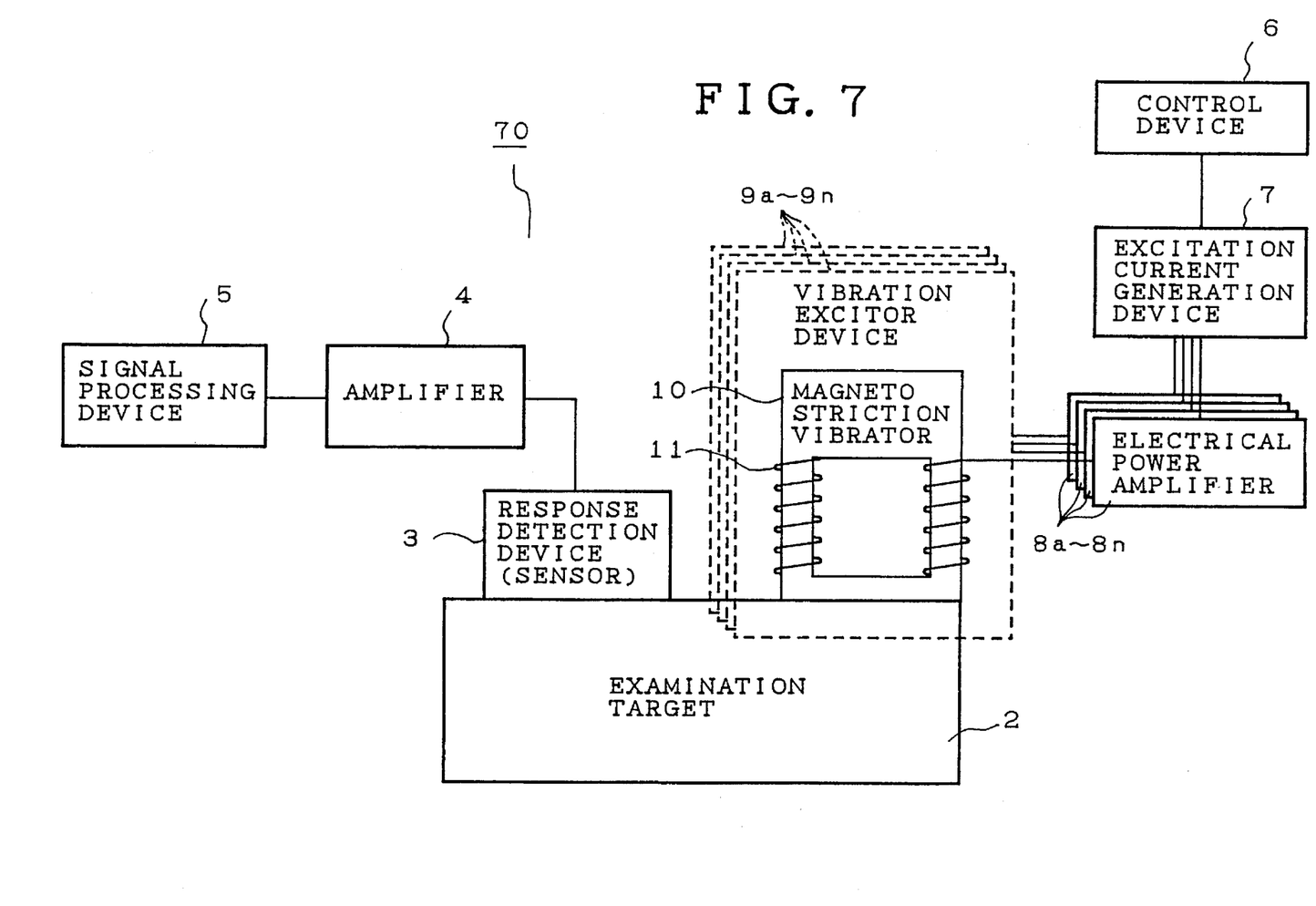
FIG. 7 is a block diagram showing a configuration of a non-destructive examination device as a third embodiment of the present invention.

FIG. 7 is a block diagram showing a configuration of a non-destructive examination device 70 as a third embodiment of the present invention. In FIG. 7, the configuration components that are the same as the configuration components of the non-destructive examination device 20 as the first embodiment shown in FIG. 2 are designated by the same reference numbers and the explanations therefor are omitted here.

In the non-destructive examination device 70 shown in FIG. 7, reference numbers 8a to 8n designate a plurality of electric power amplifiers having the same function, each of which is provided and connected to one of a plurality of vibration exciter devices 9a to 9n.

Although each of the magnetic striction vibrators 10 generates a strain having an amplitude according to the magnitude of the excitation current to be supplied, the increasing rate of the strain of each of the magnetic striction vibrators 10 is decreased when increasing the magnitude of the excitation current. Finally, a saturation point of the strain of each magnetic striction vibrator 10 is reached, where there is no increasing of the strain in each magnetic striction vibrator 10.

Like the non-extractive examination device 70 of the third embodiment shown in FIG.7, the excitation current generated by the excitation current generation device 7 is received by the plurality of the power amplifiers 8a to 8n. Then the plurality of the power amplifiers 8a to 8n amplify the excitation current at the same time and provide them to the plurality of vibration exciter devices 9a to 9n. Thereby the plurality of the vibration exciter devices 9a to 9n generate vibrations and add them to the examination target 2. In this case, the vibration greater than the vibration obtained from the saturation point of the strain of one magneto striction vibrator 10 can be achieved by the vibration excitor devices 9a to 9n of the third embodiment shown in FIG. 7. In other words, when increasing the number of the vibration excitor devices and the examination target requires a vibration more than the magnitude of vibration provided at the saturated point of one magneto striction vibrator to be detected correctly, a response waveform having a desired amplitude generated by the examination target 2 can be obtained.

Fourth Embodiment

Figure 8:
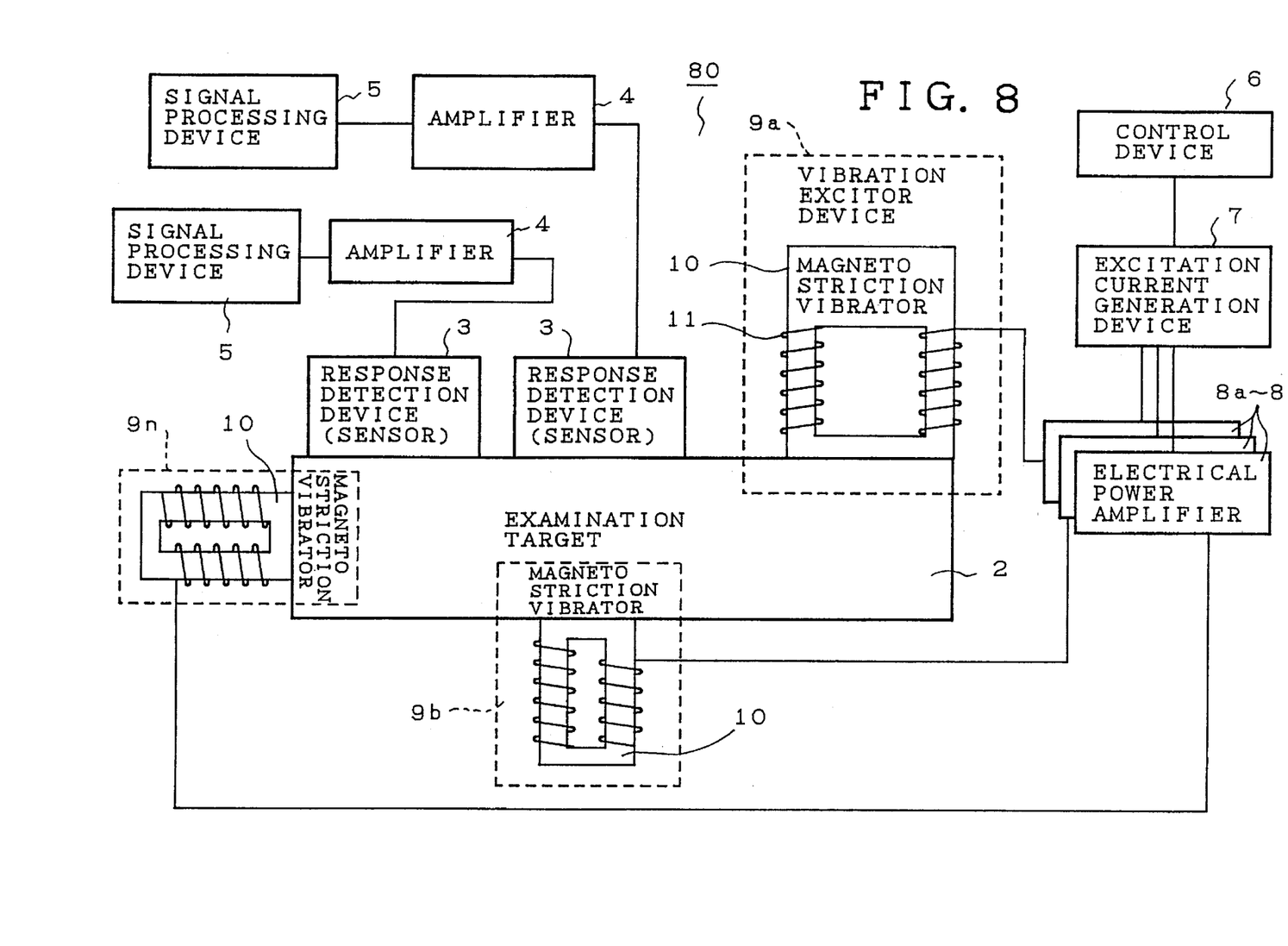
FIG. 8 is a block diagram showing a configuration of a non-destructive examination device as a fourth embodiment of the present invention.

FIG. 8 is a block diagram showing a configuration of a non-destructive examination device as a fourth embodiment of the present invention. In FIG. 8, the configuration components that are the same as the configuration components of the non-destructive examination device 60 as the third embodiment shown in FIG. 7 are designated by the same reference numbers and the explanations therefor are omitted here.

In the non-destructive examination device 80 shown in FIG. 8, a plurality of the vibration excitor devices 9a to 9n are bonded on different points on the examination target 2. In this embodiment, the examination target 2 is vibrated at the different points at the same time by the plurality of the vibration excitor devices 9a to 9n in order to generate a required vibration mode in the examination target 2. Therefore complicated vibration mode analyses can be performed by using the non-destructive examination device 80 of the fourth embodiment without any limitation of the shape of the examination target 2. In addition, the number of the response detector devices 3 or as a sensors can be increased. In this case, a pair of the amplifier 4 and the signal processing device 5 must be provided for each response detection device 3 or each sensor.

In the non-destructive examination devices 20, 60, 70, and 80 described above, as shown in FIGS. 2, 6, 7, and 8, the magneto striction vibrator 10 is vibrated and strained by using the excitation current pulse, it can be not limited by this. The form of the excitation current may be a rectangular wave, or triangular wave and the like. By using the rectangular wave and the triangular wave of the excitation current, the same effect of the first to fourth embodiments described above can be obtained. Specifically, when the triangular wave of the excitation current is used, the amplitude of the vibration can be increased so that more strongly vibration force can be generated by the magneto striction vibrator.

As it is described above in detail that the configurations and the operations of the non-destructive examination devices of the preferred embodiments according to the present invention, by using the non-destructive examination device, the elastic wave is generated by the vibration excitor device in accordance with the excitation current from the excitation current generation device, and then the response signal from the examination target which has been vibrated by the elastic wave is detected by the response detector device or the sensor. The signal processing device processes the response signal from the response detector to obtain the required detection data. Accordingly, the magnitude, the frequency, and the waveform of the vibration to be added to the examination target can be controlled with desired values, so that a constant magnitude force of the vibration can be added to the examination target in order to obtain a vibration excitor result with a high accuracy.

In addition, by using the non-destructive examination device of the present invention, the excitation current pulse is supplied to the vibration exciter device, so that a rapid impact vibration whose force is more than that of the impact hammer can be added to the examination target.

Furthermore, because a sine wave of the excitation current is supplied to the vibration exciter device, the amplitude of the excitation current can be increased in order to generate the vibration force to the examination target.

In addition, in the non-destructive examination device of the present invention, the response detection signal from the response detection device is added and averaged at the constant time interval by using the excitation current as a trigger, so that a Signal/Noise (S/N) ratio can be increased.

Finally, by using the non-destructive examination device of the present invention, the excitation current is provided to a plurality of vibration excitor devices and the plurality of vibration excitor devices generates elastic waves which are in synchronism with each other, so that a vibration force having a great magnitude can be added to any desired point on the examination target. In addition, the results of the vibration excitor examination with a higher accuracy can be obtained because a plurality of points on the examination target can be vibrated at the same time and in synchronization with each other.

Although the present invention has been described and illustrated in detail, it is clearly understood that the same is by way of illustration and example only and is not to be taken by way of limitation, the spirit and scope of the present invention being limited only by the term of the appended claims.

What is claimed is:

1. A non-destructive examination device, comprising:
   excitation current generation means for generating an excitation current and supplying said excitation current;

control means for generating a control signal to control operation of said excitation current generation means and for transmitting said control signal to said excitation generation means;

vibration excitor means for receiving said excitation current and for generating an elastic wave in accordance with a magnitude of said excitation current and for vibrating an examination target to be examined by using said elastic wave;

response detection means for detecting a vibration of said examination target responding to said elastic wave and for transforming said vibration to an electrical signal and for providing said electrical signal;

signal processing means for receiving said electrical signal and for processing said electrical signal in order to obtain desired examination information; and amplifier means located between said excitation current generation means and said vibration excitor means for amplifying said excitation current and for generating an excitation current having a desired magnitude, and for providing said amplified excitation current to said vibration excitor means;

wherein said signal processing means receives said excitation current generated by said excitation current generation means, and adds and averages said electrical signal provided from the response detection means at a constant timing rate in accordance with the vibration of said vibration excitor means imparted to said examination target, based on a trigger generated when said excitation current is detected.

2. A non-destructive examination device as claimed in claim 1, wherein
said excitation current generation means provides said excitation current of a pulse phase to said vibration excitor means in accordance with said control signal.

3. A non-destructive examination device as claimed in claim 1, wherein
said excitation current generation means provides said excitation current of a sine wave phase to said vibration excitor means in accordance with said control signal.

4. A non-destructive examination device as claimed in claim 1, wherein
said excitation current generation means provides said excitation current of a rectangular wave phase to said vibration excitor means in accordance with said control signal.

5. A non-destructive examination device as claimed in claim 1, wherein
said excitation current generation means provides said excitation current of a triangular wave phase to said vibration excitor means in accordance with said control signal.

6. A non-destructive examination device as claimed in claim 1, wherein
said vibration excitor means comprises a plurality of vibration excitor devices which have a same configuration and a same function, said excitation current generation means provides said excitation current to said plurality of vibration excitor devices, said plurality of vibration excitor devices receives said excitation current in synchronization with each other, and each of said plurality of vibration excitor devices generates said elastic wave in accordance with said excitation current.

7. A non-destructive examination device as claimed in claim 6, further comprises a plurality of amplifier means located between said excitation current generation means and said plurality of vibration excitor devices, each of said plurality of amplifier means connected to one of said plurality of vibration excitor devices, said plurality of amplifier means amplifying said excitation current and each of said plurality of amplifier means generating an excitation current having a desired magnitude and providing said amplified excitation current to one of said plurality of vibration excitor devices.

8. A non-destructive examination device as claimed in claim 1, wherein
said vibration excitor means comprises a magneto striction vibrator having a hollow body and an excitation coil wound around said hollow body, and said magneto striction vibrator vibrates when said excitation current flows in said excitation coil.

9. A non-destructive examination device as claimed in claim 8, wherein
a resonant frequency of said excitation current flowing through said excitation coil is determined by a propagation speed of said vibration propagated in said magneto striction vibrator and a shape of said magneto striction vibrator.

10. A non-destructive examination device as claimed in claim 9, wherein
a full length of said magneto striction vibrator is a multiple of a ¼ wavelength of said resonant frequency.

11. A non-destructive examination device as claimed in claim 8, wherein
said magneto striction vibrator having a laminate structure comprises a plurality of thin plates of a magneto striction material, and a laminate direction of said plurality of thin plates of said magneto striction vibrator and a vibration direction of said magneto striction vibrator cross at right angles.

12. A non-destructive examination device as claimed in claim 11, wherein
said magneto striction vibrator has a laminate structure comprises a plurality of thin plates of a magneto striction material of Nickel (Ni).

13. A non-destructive examination device as claimed in claim 11, wherein
said magneto striction vibrator has a laminate structure comprises a plurality of thin plates of a magneto striction material of Cobalt-Iron (Co-Fe).

14. A non-destructive examination device as claimed in claim 1, wherein
the magnitude and the frequency of said excitation current is changed by said control signal generated by said control means.

15. A non-destructive examination device, comprising:
excitation current generation means for generating an excitation current and supplying said excitation current;

control means for generating a control signal to control operation of said excitation current generation means and for transmitting said control signal to said excitation generation means;

vibration excitor means for receiving said excitation current and for generating an elastic wave in accordance with a magnitude of said excitation current and for vibrating an examination target to be examined by using said elastic wave;

response detection means for detecting a vibration of said examination target responding to said elastic wave and for transforming said vibration to an electrical signal and for providing said electrical signal;

signal processing means for receiving said electrical signal and for processing said electrical signal in order to obtain desired examination information; and said signal processing means receives said excitation current generated by said excitation current generation means, and adds and averages said electrical signal provided from the response detection means at a constant timing rate in accordance with the vibration of said vibration excitor means imparted to said examination target, based on a trigger generated when said excitation current is detected.

* * * * *